United States Patent [19]

Roehl

[11] 4,346,079

[45] Aug. 24, 1982

[54] SOLID ANTIPERSPIRANT COMPOSITION AND PROCESS FOR ITS PREPARATION

[75] Inventor: Ernst-Ludwig Roehl, Naarden, Netherlands

[73] Assignee: Naarden International N.V., Naarden-Bussum, Netherlands

[21] Appl. No.: 203,374

[22] Filed: Nov. 3, 1980

[30] Foreign Application Priority Data

Nov. 7, 1979 [NL] Netherlands .................. 7908149

[51] Int. Cl.³ .................. A61K 7/34; A61K 7/36; A61K 7/38
[52] U.S. Cl. .................. 424/65; 424/DIG. 5; 424/66; 424/68
[58] Field of Search .................. 424/65, DIG. 5

[56] References Cited

U.S. PATENT DOCUMENTS

| | | | |
|---|---|---|---|
| 3,259,545 | 7/1966 | Teller | 424/DIG. 5 |
| 3,903,258 | 9/1975 | Siegal | 424/DIG. 5 |
| 3,987,189 | 10/1976 | Andree et al. | 424/DIG. 5 |
| 4,011,311 | 3/1977 | Noomen et al. | 424/DIG. 5 |
| 4,154,816 | 5/1979 | Roehl et al. | 424/DIG. 5 |

FOREIGN PATENT DOCUMENTS 7512239 10/1975 Netherlands .

OTHER PUBLICATIONS

Kunimura et al., Chem. Abs., 1976, vol. 85, 10309b, for "Transparent Solid Ointment Bases".
Fujii, Chem. Abs., 1975, vol. 83, 136721g, for "Transparent Gelled Alcohols".

*Primary Examiner*—Dale R. Ore
*Attorney, Agent, or Firm*—Brumbaugh, Graves, Donohue & Raymond

[57] ABSTRACT

Antiperspirant compositions containing dibenzyl sorbitol as a gelling agent and only up to 10% of a propylene - ethylene glycol polycondensate and process for preparing said compositions.

10 Claims, No Drawings

SOLID ANTIPERSPIRANT COMPOSITION AND PROCESS FOR ITS PREPARATION

The invention relates to a means for preventing perspiration and a process for its preparation. More specifically the invention relates to such a means in solid state for instance a stick, with a transparent appearance.

Known antiperspirant sticks consist largely of a gelled alcoholic solution of an antiperspirant compound, the gelling agent therein consisting of sodium salts of higher fatty acids like sodium stearate. However such sticks cannot contain the most usual antiperspirant compounds because the acidic reaction of these compounds causes decomposition of the soap. To avoid this defect, alkaline reacting antiperspirant compounds were developed, like aluminum hydroxy chloride sodium lactate-complex, but they suffer from the disadvantage of having a poor antiperspirant effect (vide e.g. E. L. Roehl, Seifen, Öle, Fette, Wachse 99 (1973) no. 6/7 page 155 and P. Mannheim, Soap Perfumery and Cosmetics 39 (1966), no. 10, page 807). On the other hand, antiperspirant sticks are also known which are formulated with the usual, acidic reacting antiperspirant compounds. These sticks are prepared from mixtures of solid and liquid waxes, but they lack the transparent appearance of a gelled stick that is so attractive to the consumer. Moreover these sticks are difficult to prepare because often undesirable changes in shape occur on solidification of the warm liquid mass, after having been poured in the molds.

Furthermore from the Dutch Patent Application No. 75.12239 laid open to public inspection it is known to prepare solid transparent gelled antiperspirant compositions containing acidic reacting antiperspirant compounds by causing a solution of this compounds in a mixture of mono- and polyhydric alcohols to gel with the aid of dibenzaldehyde-monosorbitol acetal and a polypropylene glycol/ethylene glycol polycondensate. Although one would expect that dibenzaldehyde-monosorbitol acetal (indicated below by the name dibenzyl sorbitol) would not be stable in the acidic medium supplied by the antiperspirant compound it was nevertheless found to be possible to obtain a stable gelled composition in this way.

The aforesaid patent application claims rights for antiperspirant compositions of the following formulation:
10-80% by weight of lower monohydric alcohols,
10-60% by weight of dihydric and/or trihydric polyols or lower polyglycols,
5-30% by weight of a propylene-ethylene glycol polycondensate having the formula $HO(C_2H_4O)_x(C_3H_6O)_yH$, wherein $$\frac{y}{x+y}$$

is 0.6-1, the polycondensate having an average molecular weight of at least 500,
0.5-5% by weight of dibenzyl sorbitol,
2-15% by weight of antiperspirant metal compounds, and
0-10% by weight of mono- or dialkylol amide of higher fatty acids.

It has been found that the stability of the dibenzyl sorbitol in the above composition is related to the hydrophobic character thereof. An additional advantage of the hydrophobic character is the decrease in irritation caused by the antiperspirant composition with persons having a sensitive skin.

However, the aforesaid antiperspirant gels have the drawback that upon application on the skin they cause a sticky feel, this being experienced by the consumer as unpleasant.

It has now been found that the stickiness of the gels described in the said Dutch Patent Application No. 75.12239 may be avoided by the following two measures:

(a) The high molecular hydrophobic polycondensate of propylene glycol and ethylene glycol can be omitted entirely or for a large part thereof. Although the obtained gel then does not possess a hydrophobic character or will possess only a slightly hydrophobic character it has surprisingly been found that the dibenzyl sorbitol present therein is nevertheless not subject to hydrolysis and that the gel is stable.

(b) There may be added substances having an oily feel on the skin which substances will therefore be indicated below as oleaginous compounds. Upto the present these compounds have been used for skin care purposes and softening the skin and are therefore used in skin care preparations such as hand creams and ointments, body lotions, cream bath oils, baby oils and baby ointment. However it was not known that these compounds are capable of lessening the stickiness of solid antiperspirant compositions.

The invention therefore relates to solid transparent gelled antiperspirant compositions containing lower monohydric alcohols, dihydric and/or trihydric alcohols, or lower polyglycols, dibenzyl sorbitol, antiperspirant metal compounds and monoalkylolamides or dialkylolamides of higher fatty acids, said compositions being characterized in that the gel consists of the following components in the indicated amounts expressed in percentages by weight:

|  |  | preferred |
| --- | --- | --- |
| lower monohydric alcohols | 5-80 | 10-60 |
| dihydric and/or polyhydric alcohols and/or polyglycols and/or (poly)glycolethers having at least one remaining OH—radical | 5-75 | 20-40 |
| dibenzyl sorbitol | 0.5-10 | 1-3.5 |
| mono- and/or dialkylolamides of higher fatty acids | 0-15 | 2-10 |
| oleaginous compounds for stickiness-control | 0-25 | 2-10 |
| antiperspirant metal compounds | 2-20 | 4-10 |
| higher fatty acid | 0-1 | 0.1-0.5 |

Although the gels may be prepared without the oleaginous compounds for stickiness control it is preferred that said compositions contain at least 0.1% by weight of these compounds and in particular from 2 to 10% by weight.

Like indicated above it is possible to prepare stable gels without utilizing the propylene glycol-ethylene glycol polycondensate added in accordance with the Dutch Patent Application No. 75.12239. Where it may be recommendable sometimes to impart a somewhat hydrophobic character to the gel in order to decrease the chance of a skin irritation the polycondensate may be added in an amount of at most 10% by weight and preferably of no more than 5% by weight.

As will be apparent from the above the degree of stickiness is dependent on the added amount of oleaginous compounds and polycondensate while if desired it is meanwhile possible to combine the desired slight stickiness with a certain degree of hydrophobic character by adjusting the mutual ratio thereof.

As oleaginous compounds for stickiness control the following may be used:

(a) Esters of monohydric or polyhydric alcohols with monobasic or polybasic carboxylic acids. These esters may be either saturated or unsaturated, have an aliphatic character and be straight or branched chained or contain alicyclic or aromatic rings, while they may have additional functional groups like hydroxyl or carbonyl groups; examples of these esters are: aliphatic esters of adipic acid, citric acid, lactic acid, acetylated citric acid and acetylated lactic acid, esters of aliphatic carboxylic acids with ethylene glycol and propylene glycol;

(b) siloxanes having a viscosity of from 0.01 to 25 centistokes, preferably of from 0.1–10 centistokes, for example: polydimethylsiloxanes, polyphenylmethyl siloxanes, cyclic polydimethyl siloxanes;

(c) hydrocarbons boiling at a maximum of 350° C./1 atmosphere gage pressure; in particular branched chained hydrocarbons.

(d) Branched chained and/or unsaturated fatty alcohols being liquid at room temperature like lauryl alcohol, oleylalcohol, linoleic alcohol, linolenic alcohol and 2-octyldodecanol.

Likewise very useful are mixtures of compounds selected from the groups a, b, c and d.

These oleaginous compounds should be homogeneously miscible with the solvent blend contained in the gel. Moreover these compounds should be tolerated well by the skin.

The polycondensate to be added optionally should have an average molecular weight of at least 500 and preferably of from 1500–2000 and should be composed of at least 60% and preferably of from 80 to 90% of propylene-oxygroups.

The lower monohydric alcohols are preferably alcohols containing at most 4 carbon atoms. Ethanol and isopropanol in particular are very well suitable. Examples of dihydric and polyhydric alcohols, polyglycols and (poly)glycol ethers are: 1,2-propylene glycol, 1,3-butylene glycol, hexylene glycol, diethylene glycol, triethylene glycol, dipropylene glycol, 2-methoxyethanol, 2-ethoxyethanol, 2-butoxyethanol, diethylene glycol monomethyl ether, diethylene glycol monoethyl ether, diethylene glycol monobutyl ether, triethylene glycol monoethyl ether, polycondensates of propylene glycol, polycondensates of ethylene glycol, copolycondensates of propylene glycol and ethylene glycol.

The alkylolamides of higher fatty acids are added in order to improve the stability of the gel. There may be mentioned alkylol amides of fatty acids containing 8–24 carbon atoms. Very suitable are also blends of fatty acid alkylol amides like the alkylol amides of the fatty acid mixture derived from coconut oil. It is preferred to use the monoalkylol amides such as monoethanol amides in the gels according to the invention.

The antiperspirant metal compounds may be the usual compounds of aluminum, zinc, and zirconium, especially aluminum hydroxy chlorides and bromides; the aluminum hydroxy chlorides being preferred. Optionally these compounds may be used in the form of a complex, for example with propylene glycol, or in the form of a solution in an alcohol prepared in advance.

Upon heating, solutions of aluminum hydroxy chlorides have the tendency to gel prematurely thus hampering the further use thereof. This premature gelling may be suppressed effectively by the addition of a small amount of a higher fatty acid like stearic acid without detrimentally affecting the stability of the antiperspirant gel in ready condition.

Furthermore a de-odorant effect may be imparted to the composition according to the invention by the addition of a suitable bactericidal compound for example a chlorophenol like hexachlorophene or 2,4,4'-trichloro 2'-hydroxydiphenyl ether in a amount of preferably at most 2%.

To improve the attractiveness of the product to the consumer a perfume may be added in an amount preferably amounting to no more than 5% as well as a colorant, if desired.

In preparing the composition according to the invention all components may be mixed and heated to obtain a clear and homogeneous solution, this solution being subsequently poured into molds and cooled.

The way and the sequence in which the components of the composition are mixed is not critical. Preferably however, the metal compound is previously dissolved separately in part of the solvents (lower monohydric alcohol and/or lower polyhydric alcohol) and this solution is then added to the solution of the remaining components in the remainder of the solvents.

The example illustrates the preparation of a composition according to the invention but does not limit the scope thereof.

EXAMPLE

Antiperspirant sticks having different compositions like indicated in the following table under the numbers 1–8, inclusive, were prepared in a manner indicated below:

|   |   | 1 | 2 | 3 | 4 | 5 | 6 | 7 | 8 |
|---|---|---|---|---|---|---|---|---|---|
| A | 1,2-propylene glycol | 28.7 | 8.5 | — | 35.2 | 6.2 | 12.0 | 20.0 | 20.0 |
|   | hexylene glycol | — | 34.5 | 20.2 | — | 28.2 | 17.6 | 12.2 | 14.2 |
|   | dipropylene glycol | — | — | 20.0 | — | — | — | — | — |
|   | polyethylene glycol 400 (x) | — | 1.0 | — | — | — | — | — | — |
|   | propylene-ethylene glycol polycondensate | 15.0 | — | — | 4.0 | — | — | — | — |
|   | coco fatty acid monoethanol amide | 3.0 | 2.0 | 6.0 | 3.0 | 4.0 | 6.0 | 4.0 | 4.0 |
|   | dibenzyl sorbitol | 2.0 | 2.2 | 2.0 | 2.0 | 1.8 | 2.1 | 2.0 | 2.0 |
|   | triethyl citrate | — | — | — | — | 8.0 | — | 6.0 | — |
|   | glycerol diacetate | — | — | — | — | — | 4.0 | — | — |
|   | polydimethyl siloxane, 3 centistokes | — | — | — | 4.0 | — | — | 4.0 | — |
|   | aliphatic isoparaffin, boiling range 168–190° C. | — | — | — | — | — | 1.0 | — | — |
|   | lauryl alcohol | — | — | — | — | — | — | — | 8.0 |
|   | 2,4,4'-trichloro-2'-hydroxydiphenylether | 0.3 | 0.3 | 0.3 | 0.3 | 0.3 | 0.3 | 0.3 | 0.3 |
| B | aluminum hydroxy chloride | 10.0 | 10.0 | 10.0 | 10.0 | 10.0 | 10.0 | 10.0 | 10.0 |
|   | ethanol, 96–99% | 40.0 | 40.0 | 40.0 | 40.0 | 40.0 | 40.0 | 40.0 | 40.0 |
|   | stearic acid | 0.5 | 0.5 | 0.5 | 0.5 | 0.5 | 0.5 | 0.5 | 0.5 |

| -continued | 1 | 2 | 3 | 4 | 5 | 6 | 7 | 8 |
|---|---|---|---|---|---|---|---|---|
| perfume composition | 1.0 | 1.0 | 1.0 | 1.0 | 1.0 | 1.0 | 1.0 | 1.0 |
| TOTAL | 100% | 100% | 100% | 100% | 100% | 100% | 100% | 100% |

All amounts are expressed in percentages by weight.
(x) polyethylene glycol having an average molecular weight of 400.

The components indicated under A were heated together until a homogeneous mixture was obtained. This mixture was then cooled to about 100° C.

The stearic acid and the perfume composition were dissolved in the proper amount of a marketed ready for use 20% solution of aluminum hydroxy chloride in ethanol by heating to a temperature of 70° C. Thereupon this solution was added to the hot mixture A. The total mixture then was at a temperature of about 75° C. This total mixture was poured into molds and cooled.

All eight types of antiperspirant sticks showed excellent antiperspirant properties and an easy applicability on the skin. No one of the eight sticks did cause any irritation of the skin. Upon use of the stick 1 made in accordance with the Dutch Patent Application No. 75.12239 the skin did not loose an inconvenient sticky feel. The sticks 2 and 3 exhibited this disadvantage in a much lesser degree whereas in case of stick 4 this drawback was hardly perceivable. The sticks 5–8, inclusive, did not cause any sticky feel on the skin at all.

I claim:

1. In a solid transparent gelled antiperspirant composition comprising
   (a) 5–80% by weight of a lower monohydric alcohol,
   (b) 5–75% by weight of a dihydric alcohol, a polyhydric alcohol, a polyglycol or a polyglycol ether having at least one hydroxyl radical, or a mixture of two or more thereof,
   (c) 0.5–10% by weight of dibenzaldehydemonosorbitol acetal,
   (d) 0–15% by weight of a monoalkylolamide or dialkylolamide of a higher fatty acid,
   (e) 0–10% by weight of a propylene-/ethylene glycol polycondensate having an average molecular weight of at least 500 and composed of at least 60% propyleneoxygroups,
   (f) 2–20% by weight of a metal antiperspirant compound, and
   (g) 0–1% by weight of a higher fatty acid, wherein the improvement comprising incorporating 0.1 to 25% by weight of an oleaginous compound to lessen stickiness of said composition, said oleaginous compound selected from the group consisting of an ester of a monohydric alcohol with a monobasic carboxylic acid, an ester of a monohydric alcohol with a polybasic carboxylic acid, an ester of a polyhydric alcohol with a monobasic carboxylic acid, an ester of a polyhydric alcohol with a polybasic carboxylic acid, a siloxane having a viscosity of 0.01 to 25 centistokes, a hydrocarbon having a boiling point of a maximum of 350° C. at one atmosphere pressure, saturated fatty alcohols being liquid at room temperature, unsaturated fatty alcohols being liquid at room temperature, and a mixture of two or more compounds of said group.

2. The composition of claim 1 wherein
   (a) said ester of a monohydric alcohol or polyhydric alcohol with a monobasic or polybasic carboxylic acid is selected from a group consisting of aliphatic esters of adipic acid, citric acid, lactic acid, acetylated citric acid, acetylated lactic acid and esters of aliphatic carboxylic acids with ethylene glycol and propylene glycol,
   (b) said siloxane having a viscosity of 0.1 to 10 centistokes, which is selected from the group consisting of polydimethylsiloxanes, polyphenylmethyl siloxanes, and cyclic polydimethyl siloxanes,
   (c) said hydrocarbon is a branched chained hydrocarbon,
   (d) said saturated alcohol is selected from the group consisting of lauryl alcohol and 2-octyldodecanol, and
   (e) said unsaturated alcohols selected from the group consisting of oleylalcohol, linoleic alcohol, and linolenic alcohol.

3. The composition of claim 1 wherein said oleaginous compound is present in an amount of from 2–10% by weight.

4. The composition of claim 1 wherein said composition is a stick.

5. The composition of claim 1 further comprising up to 2% by weight of a bactericide and up to 5% by weight of a perfume.

6. The composition of claim 1 wherein (a), (b), (c), (d), (e), (f) and (g) are present in the following amounts:
   (a) 10–60% by weight of a lower monohydric alcohol,
   (b) 20–40% by weight of a dihydric alcohol, a polyhydric alcohol, a polyglycol or a polyglycol ether having at least one hydroxyl radical, or a mixture of two or more thereof.
   (c) 1–3.5% by weight of dibenzaldehydemonosorbitol acetal,
   (d) 2–10% by weight of a monoalkylolamide or dialkylolamide of a higher fatty acid,
   (e) 0–5% by weight of a propylene-/ethylene glycol polycondensate having an average molecular weight of at least 500 and composed of at least 60% propyleneoxygroups,
   (f) 4–10% by weight of a metal antiperspirant compound, and
   (g) 0.1–0.5% by weight of a higher fatty acid.

7. The composition of claim 1 wherein
   (a) said monohydric alcohol mentioned in component (a) is selected from the group consisting of ethanol and isopropanol,
   (b) said polyglycol mentioned in component (b) is selected from a group consisting of condensation polymers of propylene glycol, condensation polymers of ethylene glycol, or a condensation copolymer of propylene glycol and ethylene glycol,
   (c) said dihydric alcohol mentioned in component (b) is selected from the group consisting of 1,2-propylene glycol and 1,3-butylene glycol,
   (d) said monoalkylolamide or dialkylolamide is a monoalkylolamide or dialkylolamide of a fatty acid having 8–24 carbon atoms,
   (e) said propylene glycol/ethylene glycol polycondensate consists of 80 to 90% of propylene-oxy groups and has an average molecular weight of 1500 to 2000, (f) said metal antiperspirant compound is selected from the group consisting of an aluminum hydroxychloride, an aluminum hydroxybromide, a complex of one or more of said compounds with propylene glycol, or a solution of one or more of said compounds in alcohol, and (g) said higher fatty acid is stearic acid.

8. The composition of claim 7 further comprising up to 2% by weight of a bactericide and up to 5% by weight of a perfume.

9. A process for preparing an improved solid transparent gelled antiperspirant composition comprising:
(a) 5–80% by weight of a lower monohydric alcohol,
(b) 5–75% by weight of a dihydric alcohol, a polyhydric alcohol, a polyglycol or a polyglycol ether having at least one hydroxyl radical, or a mixture of two or more thereof,
(c) 0.5–10% by weight of dibenzaldehydemonosorbitol acetal,
(d) 0–15% by weight of monoalkylolamide or dialkylolamide of a higher fatty acid,
(e) 0–10% by weight of a propylene/ethylene glycol polycondensate having an average molecular weight of at least 500 and composed of at least 60% propyleneoxygroups,
(f) 2–20% by weight of a metal antiperspirant compound, and
(g) 0–1% by weight of a higher fatty acid, wherein the improvement comprising incorporating 0.1 to 25% by weight of an oleaginous compound to lessen stickiness of said composition, said oleaginous compound selected from the group consisting of an ester of a monohydric alcohol with a monobasic carboxylic acid, an ester of a monohydric alcohol with a polybasic carboxylic acid, an ester of a polyhydric alcohol with a monobasic carboxylic acid, an ester of a polyhydric alcohol with a polybasic carboxylic acid, a siloxane having a viscosity of 0.01 to 25 centistokes, a hydrocarbon having a boiling point of at most 350° C. at one atmosphere pressure, saturated fatty alcohols being liquid at room temperature, unsaturated fatty alcohols being liquid at room temperature, and a mixture of one or more compounds of said group, comprising mixing together said oleaginous compound and said components (a) through (g), heating the mixture thus formed to obtain a clear and homogeneous solution, pouring said solution into molds, and cooling said molds.

10. A process according to claim 9 wherein said mixing step comprises forming a first solution of said component (f) in a portion of said component (a), in a portion of said component (b), or in a mixture of portions of said components (a) and (b), forming a second solution of said oleaginous compound, components (c), (d), (e) and (g) and the portions of (a) and (b) which are not in said first solution, and mixing together said first and second solutions.

* * * * *